United States Patent [19]
Shirai et al.

[11] B 3,994,962
[45] Nov. 30, 1976

[54] METHOD OF MANUFACTURING OPTICALLY ACTIVE P-HYDROXYPHENYLGLYCINE

[75] Inventors: Tadashi Shirai, Musashino; Yasuhisa Tashiro, Yokohama; Shigeru Aoki, Tokyo, all of Japan

[73] Assignee: Nippon Kayaku Kabushiki Kaisha, Tokyo, Japan

[22] Filed: Jan. 28, 1975

[21] Appl. No.: 544,899

[44] Published under the second Trial Voluntary Protest Program on February 17, 1976 as document No. B 544,899.

[30] Foreign Application Priority Data

Jan. 29, 1974  Japan.............................. 49-11423
May 8, 1974    Japan.............................. 49-50993

[52] U.S. Cl............................ 260/501.12; 260/519
[51] Int. Cl.²..................................... C07C 143/28
[58] Field of Search................................ 260/501.12

[56] References Cited

UNITED STATES PATENTS

| 3,523,969 | 8/1970 | Chibata et al. ................ 260/501.12 |
| 3,742,041 | 6/1973 | Chibata et al. ................ 260/501.12 |

*Primary Examiner*—James O. Thomas, Jr.
*Assistant Examiner*—Nicky Chan
*Attorney, Agent, or Firm*—Russell & Nields

[57] ABSTRACT

Optically active p-hydroxyphenylglycine is manufactured by inoculating a supersaturated solution of a p-hydroxyphenylglycine sulfonic acid derivative salt comprising a mixture of the two optically active enantiomers of said salt with an optically active enantiomer of the same salt, said mixture being either racemic or else one in which the predominant enantiomer is that of the inoculant. In this manner the enantiomer having the form of the inoculant is selectively crystallized. The selectively crystallized salt is thereafter treated for removal of the sulfonic acid derivative.

6 Claims, No Drawings

METHOD OF MANUFACTURING OPTICALLY ACTIVE P-HYDROXYPHENYLGLYCINE

DETAILED DESCRIPTION OF THE INVENTION

This invention relates to a novel method of manufacturing optically active p-hydroxyphenylglycine.

Heretofore, chemical methods and biochemical methods have been proposed as techniques for the resolution of DL-p-hydroxyphenylglycine.

These chemical methods include a method (West German Pat. No. 2,147,620) which effects the resolution by causing dehydroabiethylamine, an optically active amine, to react upon N,O-diacetyl-p-hydroxyphenylglycine and utilizing the difference of solubility of the diastereoisomer salt consequently formed, and a method (J. Chem. Soc. 1971, 1920) which comprises forming a salt with quinine, an optically active amine, and thereafter, accomplishing the resolution by utilizing the difference in solubility, etc.

The biochemical methods include a method (U.S. Pat. No. 3,489,750) which obtains optically active p-hydroxyphenylglycine by asymmetrically hydrolyzing N-chloroacetyl-p-methoxyphenylglycine with hog-kidney acylase and thereafter, demethylating the resultant hydrolysate.

These methods, however, invariably fail to obtain the desired optically active p-hydroxyphenylglycine until after the resolution has been accomplished by use of a derivative and subsequently, the resolved product has been deacylated, demethylated or otherwise similarly treated. Moreover, these methods have the disadvantage, in the production of optically active p-hydroxyphenylglycine of high purity, that deacylation or demethylation usually entails racemization.

Under the circumstances, we conducted various experiments in search of processes for selective crystallization. We arrived at the discovery that the racemate of the sulfonic acid derivative salt of p-hydroxyphenylglycine of the general formula (1):

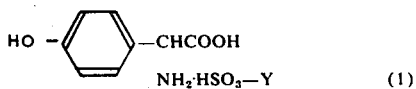

(1)

(wherein, Y represents a p-tolyl group or a 2,4-xylyl group) has a solubility in water greater than that of the optically active salt, as shown in Table 1.

Table 1

| | Solubility of sulfonic acid derivative salt of p-hydroxyphenylglycine in water (g/100 g of water) | | | |
|---|---|---|---|---|
| | p-Hydroxyphenylglycine p-toluene sulfonic acid salt | | p-Hydroxyphenylglycine m-xylene sulfonic acid salt | |
| | Racemate of sulfonic acid | Optically active salt | Racemate of sulfonic acid | Optically active salt |
| 10°C | 13.15 | 9.62 | 59.26 | 17.33 |
| 30°C | 24.89 | 13.99 | 93.27 | 34.94 |
| 50°C | 41.30 | 18.78 | | |

As a result of continued research, we found that the sulfonic acid derivative salt of DL-p-hydroxyphenylglycine can be resolved in an aqueous solvent by the selective crystallization method and further, that the optically active p-hydroxyphenylglycine can easily be obtained without entailing any appreciable racemization when the resultant sulfonic acid derivative salt of optically active p-hydroxyphenylglycine is treated by an ordinary method for the removal of sulfonic acid derivative. The present invention has been accomplished on the basis of this knowledge.

Thus, the present invention relates to a method for the manufacture of optically active p-hydroxyphenylglycine, characterized by inoculating a supersaturated solution of DL-p-hydroxyphenylglycine sulfonic acid derivative salt represented by the general formula (1) with an optically active p-hydroxyphenylglycine-sulfonic acid derivative salt to effect selective crystallization of the same type of optically active salt; or inoculating a supersaturated solution of a p-hydroxyphenylglycine sulfonic acid derivative salt having either of the two optically active salts contained therein in an excess amount over the other, with the optically active salt identical to the optically active salt existing in the excess amount in the solution to cause selective crystallization of the same type of optically active salt, collecting the selectively crystallized salt and thereafter, subjecting the salt to treatment for the removal of the sulfonic acid derivative.

To carry out the present invention, the preparation of the supersaturated solution of DL-p-hydroxyphenylglycine sulfonic acid derivative salt can be attained simply by converting DL-p-hydroxyphenylglycine sulfonic acid derivative salt or a mixture containing either of the two optically active salts in an excess amount over the other salt into a saturated solution at an elevated temperature by an ordinary method and thereafter, cooling or concentrating the resultant saturated solution. For the purpose of commercial operation, the most advantageous method is the one obtained by producing a saturated solution at an elevated temperature and then gradually cooling the resultant saturated solution so as to be converted into a supersaturated solution.

By inoculating the supersaturated solution of DL-form salt or the supersaturated solution having either of the two optically active salts contained therein in an excess amount over the other salt with crystals of the desired optically active salt, selective crystallization of the same type of optically active salt can be obtained.

Of course, the seed crystals which are used for this inoculation are required to have high purity.

Although the amount of seed crystals thus used for inoculation is desired to be as large as permissible, use of an amount corresponding to about 0.1% based on the mass of the solute involved will suffice.

Although crystallization can be attained at a temperature in the range of from 0° to 50°C, it is obtained advantageously in the neighborhood of room temperature.

As the solvent, water is best suited commercially, though water-containing organic solvents such as water-containing methanol, water-containing ethanol, water-containing acetone, etc. are also usable.

When selective crystallization of one of the two optically active salts is effected by inoculating the supersaturated solution containing one type of optically active salt in an excess amount with the same type of optically active salt, the degree of optical rotation of this solution gradually decreases in proportion as the selective crystallization of the desired optically active salt proceeds, and finally the direction of rotation is reversed.

In spite of this change of direction of rotation, the selective crystallization can be continued as before. To prevent possible inclusion of crystals of the antipode, however, the selective crystallization is preferably discontinued after the amount of crystals consequently educed has reached a total 2 to 2.5 times as large as the amount of the optically active salt which existed in excess in the dissolved state.

From the mother liquor obtained after the recovery of the crystallized optically active salt, the antipode can be obtained by converting the mother liquor into a supersaturated solution by concentration, cooling or addition of the racemate, inoculating or not said solution with the optically active salt identical to that existing in an excess amount in the mother liquor and causing selective crystallization to proceed in the same manner as described above.

The optically active p-hydroxyphenylglycine sulfonic acid derivative salt thus obtained is not optically pure. It can be converted into a highly purified optically active salt by recrystallization from water.

Then, the optically pure p-hydroxyphenylglycine sulfonic acid derivative salt is treated by the neutralization method or ion-exchange resin method, as is usually practiced, for the removal of the sulfonic acid derivative. This treatment gives birth to the optically active p-hydroxyphenylglycine.

The DL-p-hydroxyphenylglycine sulfonic acid derivative salts used by the method of this invention are novel compounds. Each can easily be obtained by mixing DL-p-hydroxyphenylglycine and the appropriate sulfonic acid derivative in equivalent weights and heating the resultant mixture in added water. Also, the resolved D- and L-p-hydroxyphenylglycine sulfonic acid derivatives are novel compounds.

Of the optically active p-hydroxyphenylglycines which are obtained by the method of this invention, the D-antipode is a highly advantageous compound as the raw material for the manufacture of semi-synthetic penicillin and semi-synthetic cephalosporin derivative.

The present invention will be described specifically herein below by the following examples.

EXAMPLE 1

With 88.4g of DL-p-hydroxyphenylglycine p-toluene sulfonic acid salt (hereinafter referred to as "DL-form salt") were mixed 17.9g of L-p-hydroxyphenylglycine p-toluene sulfonic acid salt (hereinafter referred to as "L-form salt"). The resultant mixture was dissolved in 200ml of water by heating. At 30°C the solution was inoclutaed with 0.05g of L-form salt and the solution was gently agitated at the same temperature for 1.5 hours. The resultant crystals therein, were separated from the solution by filtration, washed with water and thereafter dried. There was consequently obtained 27.16g of crude L-form salt. $[\alpha]_D^{25} = 59.97°$ (C = 2, $H_2O$). Since pure L-form salt shows $[\alpha]_D^{20} = 69.7$ (C = 2, $H_2O$), the crude L-form salt is calculated to have optical purity of 86.0%. When 25g of this crude L-form salt were recrystallized from 75ml of water, there were obtained 20.5g of optically pure L-form salt. M.p. 230°C (dec.)

Elementary analysis:
| Calculated (for $C_{15}H_{17}NO_6S$) | | Found |
|---|---|---|
| C% | 53.09 | 53.11 |
| H% | 5.05 | 5.06 |
| N% | 4.13 | 3.99 |

The L-form salt thus obtained was dissolved in 60ml of water and then neutralized with a 10% sodium carbonate aqueous solution. Consequently, there was obtained 8.76g of an optically pure L-p-hydroxyphenylglycine. $[\alpha]_D^{25} = +160.2°$ (C = 1, N-HCl).

The starting material DL-p-hydroxyphenylglycine p-toluene sulfonic acid salt was obtained as follows: With 2 ml of water, 1.67g of DL-p-hydroxyphenylglycine and 1.72 g of p-toluene sulfonic acid were mixed and dissolved by heating. When the solution was left to cool, there ensued crystallization of DL-p-hydroxyphenylglycine p-toluene sulfonic acid salt. The yield was 2.9g. M.p. 222°C (dec.)

Elementary analysis:
| Calculated (for $C_{15}H_{17}NO_6S$) | | Found |
|---|---|---|
| C% | 53.09 | 53.23 |
| H% | 5.05 | 5.05 |
| N% | 4.13 | 4.04 |

EXAMPLE 2

The mother liquor, remaining after the separation of crystals by filtration in Example 1, was mixed with 22.0g of DL-form salt and dissolved in 8.5 ml of water by heating. The solution was then kept at 30°C and, inoculated with 0.05g of D-p-hydroxyphenylglycine p-toluene sulfonic acid (hereinafter referred to as "D-form salt"), was agitated at the same temperature for 1.5 hours. By following the procedure of Example 1 from this point on, there was obtained 28.5g of crude D-form salt, $[\alpha]_D^{21} = 59.9°C$ (C = 2, $H_2O$). When this salt was recrystallized from water, there were obtained 26.5g of pure D-form salt. M.p. 229°C (dec.), $[\alpha]_D^{25} = -69.5°$ (C = 2, $H_2O$).

Elementary analysis (for $C_{15}H_{17}NO_6S$)
| Calculalted (for $C_{15}H_{17}NO_6S$) | | Found |
|---|---|---|
| C% | 53.09 | 53.18 |
| H% | 5.05 | 5.08 |
| N% | 4.13 | 3.96 |

When 25g of the D-form salt were neutralized by following the procedure of Example 1, there were obtained 10.7g of D-p-hydroxyphenylglycine. $[\alpha]_D^{25} = -160.5°$ (C = 1, N-HCl).

EXAMPLE 3

The L-form salt was crystallized in the same way as in Example 1. The mother liquor remaining after the separation of these crystals by filtration was concentrated under reduced pressure and, after evaporation of 54ml of water therefrom, kept at 30°C and, inoculated with 0.05g of D-p-hydroxyphenylglycine p-toluene sulfonic acid salt (hereinafter referred to as "D-form salt"), was agitated at the same temperature for 1.5 hours. By repeating the procedure of Example 1 from this point onward, there were obtained 20.2g of crude D-form salt. $[\alpha]_D^{21} = -37.6°$ (C = 2, $H_2O$). When this was recrystallized from water, there were obtained 9.9g of pure D-form salt. M.p. 230°C (dec.), $[\alpha]_D^{25} = -69.7$ (C = 2, $H_2O$). By neutralizing 9g of the D-form salt thus obtained in the same way as in Example 1, there were obtained 3.8g of D-p-hydroxyphenylglycine. $[\alpha]_D^{25}=-160.1°$ (C = 1, N—HCl)

EXAMPLE 4

With 65 ml of water were mixed 92.2g of DL-p-hydroxyphenylglycine m-xylene sulfonic acid salt (hereinafter referred to as "DL-form salt") and 5.0g of D-p-hydroxyphenylglycine m-xylene sulfonic acid salt (hereinafter referred to as "D-form salt"). The mixture was dissolved by heating and then cooled to 35°C and, inoculated with 0.09g of D-form salt, agitated at the same temperature for 75 minutes and thereafter filtered. Consequently, there were obtained 17.35g of the same D-form salt as that used for the inoculation. $[\alpha]_D^{27}=-33.5°$ (C = 2, H$_2$O) M.p. 180 ~ 182°C. Since the optically pure D-form salt has $[\alpha]_D^{27}=-64.75°$ (C = 2, H$_2$O), the crude D-form salt was found to have an optical purity of 51.8%.

In 10 ml of water, 15.0g of the crude D-form salt were dissolved by heating, filtered and left to stand below room temperature to induce crystallization. The crystals formed were separated by filtration, washed with water and thereafter dried. Consequently, there were obtained 5.75g of D-form. $[\alpha]_D^{27}=-64.50°$ (C = 2, H$_2$O), M.p. 191 ~ 192°C.

Elementary analysis:
| | Calculated (for C$_{16}$H$_{19}$O$_6$NS) | Found |
|---|---|---|
| C% | 54.38 | 54.04 |
| H% | 5.42 | 5.35 |
| N% | 3.96 | 3.92 |

In 15 ml of water, 5.0g of the substantially pure D-form salt were dissolved at 40°C, then neutralized with a 20% sodium carbonate aqueous solution, left to stand at room temperature for one hour, thereafter filtered, washed with water and dried. Consequently, there were obtained 2.49g of D-p-hydroxyphenylglycine. $[\alpha]_D^{22}=-158.0°$ (C = 1, N-HCl)

The DL-p-hydroxyphenylglycine m-xylene sulfonic acid salt used as the starting material was produced as follows: With 2 ml of water were mixed 1.67g of DL-p-hydroxyphenylglycine and 2.23g of m-xylene sulfonic acid. The mixture was dissolved by heating and then left to cool, with the result that there were obtained 2.2g of DL-p-hydroxyphenylglycine m-xylene sulfonic acid salt. M.p. 174~175°C (dec.)

Elementary analysis:
| | Calculated (for C$_{16}$H$_{19}$NO$_6$S) | Found |
|---|---|---|
| C% | 54.38 | 53.49 |
| H% | 5.42 | 5.50 |
| N% | 3.96 | 3.92 |

EXAMPLE 5

In the mother liquor remaining after the separation of crystals by filtration in Example 4, 20g of DL-form salt were dissolved by heating and, inoculated with 0.09g of L-form salt at 35°C, agitated at the same temperature for 60 minutes and thereafter filtered. Consequently, there were obtained 16.82g of L-form salt, $[\alpha]_D^{27}=+24.28°$ (C = 2, H$_2$O), M.p. 179°– 180°C. The crude L-form salt thus formed is calculated to have an optical purity of 37.5%. When this crude L-form salt was treated in the same way as in Example 1, there were obtained 1.68g of optically pure L-p-hydroxyphenylglycine. $[\alpha]_D^{22}=+159°$ (C = 1, N HCl)

EXAMPLE 6

By following the procedure of Example 4, there was crystallized D-form salt. The mother liquor remaining after the removal of the crystals by filtration was cooled to 15°C and, agitated at the same terperature and thereafter filtered. Consequently, there was obtained 14.2g of L-form salt. $[\alpha]_D^{27}=+31.8°$ (C = 2, H$_2$O). M.p. 179°– 180°C. By following the procedure of Example 1 from this point on, there were obtained 2.5g of optically pure L-p-hydroxyphenylglycine. $[\alpha]_D^{22}=+160°$ (C = 1, N HCl)

EXAMPLE 7

A mixture of 1.54g of DL-p-hydroxyphenylglycine and 0.15g of L-p-hydroxyphenylglycine with 1.74g of p-toluene sulfonic acid was dissolved in added water by heating. The solution, inoculated with 0.035g of L-form salt at 30°C, was agitated for 5 minutes, to cause eduction of crystals. When the crystals were separated by filtration, washed and dried, there was obtained 0.80g of crude L-form salt. $[\alpha]_D^{22}=48.3$ (C = 2, H$_2$O)

When this salt was refined with water in the same way as in Example 1, there was obtained 0.53g of L-form salt. This refined salt was dissolved in water and passed through a column packed with 2 ml of Dowex 50W X-8 (H form). The column was washed with water and then subject to elution with a 10% ammonia aqueous solution. When the resultant eluate was concentrated, treated with decolorizing carbon and thereafter neutralized with 10% hydrochloric acid, there were obtained 0.25g of optically actibe L-p-hydroxyphenylglycine. $[\alpha]_D^{21}=160.5°$ (C = 1, N-HCl).

EXAMPLE 8

In 200ml of water, 88.6g of DL-p-hydroxyphenylglycine p-toluene sulfonic acid salt were dissolved by heating. The solution, after inoculation with 0.05g of D-form salt at 30°C, was agitated at the same temperature for 1.5 hours. By repeating the procedure of Example 1 from this point on, there were obtained 7.5g of crude D-form salt. This salt was recrystallized from water and thereafter, neutralized in the same way as in Example 1. Consequently, there were obtained 2.2g of D-p-hydroxyphenylglycine. $[\alpha]_D^{25}=-160.5°$ (C = 1, N-HCl).

EXAMPLE 9

In 60 ml of water, 97.0g of DL-p-hydroxyphenylglycine m-xylene sulfonic acid salt was dissolved by heating. The solution was cooled to 35°C, at which temperature it was inoculated with 0.9g of D-form salt. Thereafter, the solution was agitated at the same temperature for 60 minutes and filtered. Consequently, there were obtained 12.3g of the same D-form salt as that used for the inoculation. $[\alpha]_D^{27}=-26.2$ (C = 2, H$_2$O).

The crude D-form salt was refined and neutralized by following the procedure of Example 1. As the result of this treatment, there were obtained 1.42g of D-p-hydroxyphenylglycine. $[\alpha]_D^{20}=-157°$ (C = 1, N-HCl).

We claim:
1. DL-p-hydroxyphenylglycine p-toluene sulfonic acid salt.
2. D-p-hydroxyphenylglycine p-toluene sulfonic acid salt.
3. L-p-hydroxyphenylglycine p-toluene sulfonic acid salt.
4. DL-p-hydroxyphenylglycine m-xylene sulfonic acid salt.
5. D-p-hydroxyphenylglycine m-xylene sulfonic acid salt.
6. L-p-hydroxyphenylglycine m-xylene sulfonic acid salt.

* * * * *